US008883987B2

(12) United States Patent
Ahn et al.

(10) Patent No.: US 8,883,987 B2
(45) Date of Patent: *Nov. 11, 2014

(54) IMMUNE STIMULATING COMPOSITION COMPRISING BACTERIAL CHROMOSOMAL DNA FRAGMENTS HAVING METHYLATED CPG SEQUENCES AND NON-TOXIC LIPOPOLYSACCHARIDES

(75) Inventors: Bo Young Ahn, Seoul (KR); Yang Je Cho, Seoul (KR); Won Il Yoo, Gyeonggi-do (KR); Sung Ho Lee, Gyeonggi-do (KR); Hye Ran Park, Seoul (KR); Dong Hyun Lee, Gyeonggi-do (KR); Na-Gyong Lee, Seoul (KR); Doo Sik Kim, Seoul (KR)

(73) Assignee: Eyegene Inc., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 11/389,357

(22) Filed: Mar. 24, 2006

(65) Prior Publication Data

US 2006/0166923 A1  Jul. 27, 2006

Related U.S. Application Data (63) Continuation-in-part of application No. 10/515,353, filed as application No. PCT/KR02/01813 on Sep. 26, 2002, now Pat. No. 7,507,802.

(30) Foreign Application Priority Data

May 22, 2002 (KR) .................................. 2002/28505

(51) Int. Cl.
| | |
|---|---|
| C07H 21/04 | (2006.01) |
| C07H 21/02 | (2006.01) |
| A61K 48/00 | (2006.01) |
| A61K 31/715 | (2006.01) |
| A61K 31/739 | (2006.01) |
| A61K 39/39 | (2006.01) |
| A61K 39/00 | (2006.01) |

(52) U.S. Cl.
CPC ....... *A61K 39/39* (2013.01); *A61K 2039/55572* (2013.01); *A61K 39/00* (2013.01); *A61K 2039/57* (2013.01); *A61K 2039/55561* (2013.01); *A61K 31/739* (2013.01)
USPC ........................................ 536/23.1; 514/44 R (58) Field of Classification Search
None
See application file for complete search history.

(56) References Cited

U.S. PATENT DOCUMENTS

| 4,454,119 | A | | 6/1984 | Fukushi |
|---|---|---|---|---|
| 4,818,817 | A | * | 4/1989 | Shoham et al. ............... 536/119 |
| 4,929,604 | A | | 5/1990 | Munford et al. |
| 5,158,939 | A | | 10/1992 | Takayama et al. |
| 5,780,448 | A | | 7/1998 | Davis |
| 6,194,388 | B1 | | 2/2001 | Krieg et al. |
| 6,207,646 | B1 | | 3/2001 | Krieg et al. |
| 6,214,806 | B1 | | 4/2001 | Krieg et al. |
| 6,339,068 | B1 | | 1/2002 | Krieg et al. |
| 6,368,604 | B1 | | 4/2002 | Hone et al. |
| 6,406,705 | B1 | | 6/2002 | Davis et al. |
| 6,426,334 | B1 | | 7/2002 | Agrawal et al. |
| 6,429,199 | B1 | | 8/2002 | Krieg et al. |
| 6,653,292 | B1 | * | 11/2003 | Krieg et al. ..................... 514/44 |
| 6,693,086 | B1 | | 2/2004 | Dow et al. |
| 2001/0044416 | A1 | | 11/2001 | McCluskie et al. |
| 2002/0064515 | A1 | | 5/2002 | Krieg et al. |
| 2002/0164341 | A1 | | 11/2002 | Davis et al. |
| 2003/0026782 | A1 | | 2/2003 | Krieg |
| 2003/0050261 | A1 | | 3/2003 | Krieg et al. |
| 2003/0050263 | A1 | | 3/2003 | Krieg et al. |
| 2003/0091599 | A1 | | 5/2003 | Davis et al. |
| 2003/0100527 | A1 | | 5/2003 | Krieg et al. |
| 2003/0191079 | A1 | | 10/2003 | Krieg et al. |
| 2003/0212026 | A1 | | 11/2003 | Krieg et al. |
| 2003/0224010 | A1 | | 12/2003 | Davis et al. |
| 2004/0009949 | A1 | | 1/2004 | Krieg |
| 2004/0053880 | A1 | | 3/2004 | Krieg |
| 2004/0067905 | A1 | | 4/2004 | Krieg |
| 2004/0087534 | A1 | | 5/2004 | Krieg et al. |
| 2004/0087538 | A1 | | 5/2004 | Krieg et al. |
| 2004/0092472 | A1 | | 5/2004 | Krieg |
| 2004/0106568 | A1 | | 6/2004 | Krieg et al. |
| 2004/0132685 | A1 | | 7/2004 | Krieg et al. |
| 2004/0142469 | A1 | | 7/2004 | Krieg et al. |
| 2004/0143112 | A1 | | 7/2004 | Krieg et al. |
| 2004/0147468 | A1 | | 7/2004 | Krieg et al. |
| 2004/0152649 | A1 | | 8/2004 | Krieg |
| 2004/0152656 | A1 | | 8/2004 | Krieg et al. |

OTHER PUBLICATIONS

Cornelie et al 2004 Scandinavian Journal of Immunology vol. 59 pp. 143-151.*
Gao et al 2001 Journal of Immunology pp. 6855-6860.*
Weiner et al 1997 Proc. Natl. Acad. Sci. USA vol. 94 pp. 10833-10837.*
Katoaka et al (Jpn. J. Cancer Res. 1992 vol. 83 pp. 244-247.*
Yasuda et al Biochemical and Biophysical Research Communications vol. 293 Apr. 2002 pp. 344-348.*
Zhang et al Journal of Leukocyte Biology vol. 54 Nov. 1993 pp. 444-450.*
(Yasuda et al Biochemical and Biophysical Research Communications vol. 293 Apr. 2002 pp. 344-348).*
Yasuda et al Biochemical and Biophysical Research Communications vol. 293 Apr. 2002 pp. 344-348).*
(Smith et al The EMBO Journal vol. 4 No. 5 pp. 1319-1326, 1985).*
(Zhang et al Journal of Leukocyte Biology vol. 54 Nov. 1993 pp. 444-450).*

(Continued)

*Primary Examiner* — Nita M Minnifield
(74) *Attorney, Agent, or Firm* — The PL Law Group, PLLC (57) ABSTRACT

The present invention relates to immune stimulating composition comprising methylated bacterial chromosomal DNA fragments and non-toxic lipopolysaccharides. The composition of the present invention can be industrially applied the effective materials for treating cancers and adjuvant.

10 Claims, 10 Drawing Sheets

(56) References Cited

OTHER PUBLICATIONS (Shoham et al US Patent No. 4,818,817 Date Apr. 4, 1989).*
Wicks et al 1995 Human Gene Therapy vol. 6 pp. 317-323.*
Yi et al., "IFN-.gamma. promotes IL-6 and IgM secretion in response to CpG motifs in bacterial DNA and oligodeoxynucleotides," J. Immunol. 156(2):558-564 (1996).
Zbar et al., Immunologic approaches to the treatment of human cancer based on a Guinea pig model, Cancer Immunol. Immunother. 1:127-137 (1976).
Gao, Jian Jun, et al., "Bacterial DNA and Lipopolysaccharide Induce Synergistic Production of TNF-.alpha. Through a Post-Transcriptional Mechanism," The American Association of Immunologies, (2001), vol. 166, pp. 6855-6860.
Gao, Jian Jun, et al., "Cutting Edge: Bacterial DNA and LPS Act in Synergy in Inducing Nitric Oxide Production in RAW 264.7 Macrophages," Cutting Edge, vol. 163, (1999), pp. 4095-4099.

* cited by examiner

IMMUNE STIMULATING COMPOSITION COMPRISING BACTERIAL CHROMOSOMAL DNA FRAGMENTS HAVING METHYLATED CPG SEQUENCES AND NON-TOXIC LIPOPOLYSACCHARIDES

This application is a continuation-in-part of U.S. application Ser. No. 10/515,353, filed Nov. 18, 2004 now U.S. Pat. No. 7,507,802, and claims benefit of Korean Application No. 2002/28505, filed May 22, 2002, each of which is incorporated herein by reference.

TECHNICAL FIELD

The present invention relates to immune stimulating composition comprising bacterial chromosomal DNA fragments having methylated CpG sequences and non-toxic lipopolysaccharides.

BACKGROUND ART

Cancer therapy developed from the 1960s has largely involved the use of surgery, radio therapeutics and chemotherapy. These treatments have shown the effect that the upward curve of cancer death rate soared up to 1973 in the U.S. becomes sluggish. However, surgery and radio therapeutics are topical treatment and so they have limitation that patients are convalescing favorably only when cancer is early blocked as local cancer. Chemotherapy is successful only if all cancer cells are completely eliminated and so chemotherapy may damage the host, normal tissue such as immune system of patients and threaten life of the old and the weak. The main purpose of immuno-therapy is to resist the cancerization by reinforcing immune surveillance. There are several trials as follows.

1) Immunological prevention; An animal of the same class was inoculated with cancer tissue to prevent homologous cancer. For example, viral leukemia of animal may be prevented using its cause virus (Morton et al. 1991, proc. am. assoc. cancer res. 2: 492:494). However, this method has never been applied to a person and it is difficult to induce cellular immunity.

2) Immunotherapy;

Active Specific Immunization

This immunization is to prevent cancer cells activating specific immune cancer supervisory cells by inoculating patients with self-cancer cells or homologous cancer cells or inactivated self- or iso-cancer cells regulated by X-ray irradiation or mitomycin-C. However, this method succeeded in animal experiment not in people. Recently, in order to enhance the expression of specific antigens in cancer tissue, various methods have been of attaching with Con-A or exposing hidden antigens by treating with neuramindase or of forming hybridoma with heterologous cells. However, the use of dendritic cells (Sprinzl et al, *Cancer Treat Rev.* 2001 August; 27 (4): 247-55) or development of other various DNA vaccine treatments (Pantuck et al, *Int J Urol.* 2001 July; 8 (7):S1-4) still have a limit in their safety and effect.

Non-Specific Immunotherapy

This immunization most spotlighted at present is used solely or with chemotherapeutic agents for treating almost all kinds of tumors. The non-specific immunotherapy means that it will not be restricted by kinds of cancer. Although various theories on its mechanism have been suggested, they are on study only it is suggested that the non-specific immunotherapy stimulate reticuloendothelial system specifically activity of lymphocytes. There is Corynebacterium as the chief material actually used in clinical tests. Picibanil (OK-432), which has been used for patients in Korea already, has been studied and produced mainly in Japanese pharmaceutical company. It has been marketed in Japan, Korea or Southeast Asia. Materials formed of Picibanil has been used in treating cancer long before. In 1968, Bush Fehleison et al., Germans, discovered that the progress of cancer ceased or previously existing cancer decreased. In 1891, Coley, surgeon in Chicago, the U.S., made mixed toxin formed of materials extracted from culture medium of streptococci, which was used for many patients.

BCG (or *Tubercle bacillus*) and Associated Material Thereof

Living BCG organism: In the 1960s, Old in the U.S. and Mathe in France reported that animal cancer could be cured by inoculating BCG. In 1970, Morton in the U.S. reported that melanoma could also be cured by inoculating BCG. As a result, BCG and its associated materials were broadly used as non-specific immunotherapy. A great amount of BCG inoculation is required to expect increasing immune response. BCG can be inoculated under the skin, directly in cancer tissue region or orally administrated. However, the oral administration of BCG is not effective for people who were inoculated with BCG in their neonatal days but came into contact with *tubercle bacillus* thereafter (BCG or *tubercle bacillus* are not absorbed in people having tuberculin positive). In the treatment using living BCG organism, there are side effects such as requiring the great amount of living BCG organism and ulcer around injection, systemic symptom like chill, fever or liver function disorder. However, in case of using the small amount to decrease the side effects, the efficacy is reduced or weak.

Unmethylated CpG DNA

Mammalian DNA is different from bacterial DNA in that they have many CpG inhibitions and cytosine of CpG dinucleotide is selectively methylated. Recently, it has been recognized that CpG motifs in bacterial DNA rapidly stimulated the polyclonal B-cells and so increased IgM secretion, and stopped the progress of cell cycle by anti-IgM antibody and powerfully inhibited the induction of apoptosis to inhibit c-myc expression and made myn, blc2 and bcl-XL mRNA expression increase to protect cells from apoptosis. In other study, it was reported that CpG motifs activated directly B-cells to increase IL-6 and IL-12 secretion within a short time. Clinical test on immune adjuvants and asthmatic treatments using synthesis oligonucleotides including CpG sequences is going in progress the CPG Company in the America.

As described above, although treatments have been developed using diverse immune regulating materials, BCG and CpG among those treatments are just applied to people. Despite broad effects of BCG, it is difficult to apply a great amount of BCG or by blood injection because of its stability. In case of CpG, synthetic oligonucleotides are too expensive.

DETAILED DESCRIPTION OF THE INVENTION

Accordingly, the object of the present invention is to provide materials for inducing immune response more stable, economic, effective and specific than the conventional ones.

There is provided immune stimulating composition comprising: bacterial chromosomal DNA fragments having methylated CpG; and non-toxic bacterial lipopolysacchrides.

It is preferable that the CpG sequences of bacterial chromosomal DNA fragments are methylated and have size ranging from 2.0 to 0.5 kb and the lipopolysaccharides have dalton ranging from 3,000 to 10,000 dalton.

It is preferable that the least amount of the methylated bacterial chromosomal DNA fragments having methylated CpG and the lipopolysaccharides may be mixed to show the effect of the present invention. Particularly, the present invention shows the increase of dose dependent efficacy in a mass ratio ranging from 500:1 to 1:500. In the above-described mass ratio, the present invention is non-toxic and economic.

It is preferable that the bacterial chromosomal DNA fragments having methylated CpG and the lipopolysaccharides are mixed by shaking.

The composition of the present invention is useful for immune adjuvants or anti-cancer treatments. These effects are shown by inducing immune activation of T-helper 1 type.

It is preferable that the bacteria in the present invention is *Escherichia coli* or mycobacteria. More preferably, the bacteria is *Escherichia coli*, particularly, *E. coli* EG0021 (KCCM-10374).

In the composition of the present invention, synergy effect by mCIA02 (bacterial chromosomal DNA having methylated CpG) may be expected in stability, cell immune induction, synergy effect by CIA05 may be expected in immune reinforcement specifically cancer treatment.

The disclosed immune stimulating and controlling composition comprising bacterial chromosomal DNA fragments having methylated CpG and non-toxic lipopolysaccharides will be described briefly.

The present inventors succeeded in effective production of methylated bacterial oligonucleotides as anticancer adjuvant and development of modified lipopolysaccharides for suitable activation as anti-cancer treatments. A new immune adjuvant, mCIA07, is finally obtained by combining the methylated bacterial DNA fragments having methylated CpG and the lipopolysaccharides.

Generally, the combination of lipopolysaccharide and DNA shows synergy effect. Lipopolysaccharide shows various responses such as serving as independent antigen of T-cells. Here, the synergy effect may cause crucial results such as sepsis.

The present inventors obtained a strain, *E. coli* EG0021, having short carbohydrate chained lipopolysaccharide from *Escherichia coli* in healthy human intestines. They deposited the strain with No. KCCM 10374 in Korea culture center of microorganisms, KCCM, located in 361-221 Hongjedong, Seodaemun-gu, Seoul, Korea, in May 2$^{nd}$, 2002. They established a method of purifying lipopolysaccharide from this strain.

*E. coli* DNA, CIA02, representing immune activation was isolated from genomic DNA of *E. coli* EG0021. mCIA02 is genomic DNA having methylated CpG of *E. coli* EG0021. The CIA02 and mCIA02 were obtained after fragmentation of the isolated DNA and general treatment.

mCIA07 was finally obtained by combination of the mCIA02 and the CIA05.

PREFERRED EMBODIMENTS OF THE PRESENT INVENTION

The disclosed immune stimulating and controlling composition comprising bacterial chromosomal DNA fragments and non-toxic lipopolysaccharides will be described in more details referring to examples below, when are not intended to be limiting.

Example 1

Isolation of Non-Toxic Strain 1-1: Screening and Isolating Mutant *E. coli* Having Short Carbohydrate Chained Lipopolysaccharide

*E. coli* EG0021 having short carbohydrate chained lipopolysaccharide was isolated from healthy human intestines, and a method of purifying lipopolysaccharide from the strain was established.

A procedure was 5 times repeated of injecting liquid-cultured single colony of *E. coli* isolated from healthy adult male intestines, into experimental animal, Balb/C mouse.

50 kinds of strains were selected therein, and one colony in the selected 50 strains was obtained from a plate. After the colony was dissolved in 4 ml of 0.9% physiological saline solution, 1 ml of the solution was moved into an eppendorf tube. The solution was treated with 2 ul of DNase I and reacted at an incubator at 37° C. for 1 hour. After treatment of DNaseI, the solution was treated with 50 ul of Rnase (10 mg/ml) and reacted at an incubator of 37° C. for 1 hour. Then, 100 ul of Proteinase K (20 mg/ml) was put therein and reacted at 37° C. overnight. Human lymphocyte cell line differentiated by GM-CSF was treated with LPS of each strain obtained therefrom. TNF-α secretion was measured and a strain having the least value was selected (see Table 1) and confirmed the molecular weight of lipopolysaccharide by electrophoresis. It was shown that the attenuated strain was not morphologically changed or in its characteristics. Lipopolysaccharides having a molecular weight ranging from 5000 to 10,000 without lipopolysaccharide ladder having a molecular weight ranging from 50,000 to 100,000 were shown in electrophoresis (see FIG. 1). This strain was called EG0021.

TABLE 1

TNF-α secretion value of *E. coli* homogenate obtained from healthy human intestines

| No. | TNF-a (pg/1 ul) |
|---|---|
| EG0001 | more (>100) |
| EG0002 | 12 |
| EG0003 | 72 |
| EG0004 | 85 |
| EG0005 | 25 |
| EG0006 | 35 |
| EG0007 | 71 |
| EG0008 | 28 |
| EG0009 | 2 |
| EG0010 | 13 |
| EG0011 | 39 |
| EG0012 | 64 |
| EG0013 | 8.8 |
| EG0014 | 9 |
| EG0015 | 70 |
| EG0016 | more (>100) |
| EG0017 | 6 |
| EG0018 | 11 |
| EG0019 | 0.3 |
| EG0020 | 80 |
| EG0021 | 0.1 |
| EG0022 | more (>100) |
| EG0023 | more (>100) |
| EG0024 | more (>100) |
| EG0025 | 53 |
| EG0026 | 12 |
| EG0027 | 4 |
| EG0028 | 76 |
| EG0029 | 92 |
| EG0030 | more (>100) |
| EG0031 | 21 |
| EG0032 | 1.2 |
| EG0033 | more (>100) |
| EG0034 | more (>100) |
| EG0035 | 7 |
| EG0036 | 87 |
| EG0037 | 0.7 |
| EG0038 | 39 |
| EG0039 | 37 |
| EG0040 | 91 |
| EG0041 | 65 |
| EG0042 | 54 |
| EG0043 | More (>100) |
| EG0044 | More (>100) |
| EG0045 | 17 |
| EG0046 | 2.1 |
| EG0047 | 3.5 |
| EG0048 | More (>100) |
| EG0049 | More (>100) |
| EG0050 | More (>100) |

Example 2

*E. coli* DNA Having Methylated CpG Perparation Method 2-1: *E. coli* Chromosomal DNA Purification

*E. coli* EG0021 was cultured by shaking in TSB (Tryptic soy broth; Difco) culture medium (30 g/L) at 37° C. for 10 hours.

After 10 L cultivation, 150 g of cells obtained by centrifugation at 8,000 G was washed in TE (10 mM Tris, pH 8.0, 25 mM EDTA) buffer solution (300 ml) and centrifuged. The cells (150 g) obtained by centrifugation was dissolved in 750 ml of lysis solution (10 mM Tris (pH 8.0), 25 mM EDTA, 100 ug/mL Lysozyme) and treated at 37° C. for 1 hour.

Thereafter, proteinase K (Sigma) was added in the solution to final concentration 100 ug/ml, and treated at 50° C. for 12 hours.

Mixing the solution with phenol/chloroform/isoamyl alcohol (25:24:1) at a ratio of 1:1 was repeated three times to obtain water layer.

*E. coli* chromosomal DNA was obtained by ethanol precipitation.

After purified *E. coli* DNA was diluted using sterile distilled water, the concentration of the *E. coli* DNA was measured at 260 nm and 280 nms with UV spectrometer.

The concentration was measured according to the following method:

$$\text{Double stranded DNA concentration (ug/ml)} = OD260 \text{ nm} \times \text{dilution rate} \times 50$$

$$\text{Single stranded DNA concentration (ug/ml)} = OD260 \text{ nm} \times \text{dilution rate} \times 40$$

$$OD260 \text{ nm}/OD280 \text{ nm} = 1.7 \sim 1.8$$

2-2: Methylation on CG Sequence of *E. coli* DNA

Figure 2:
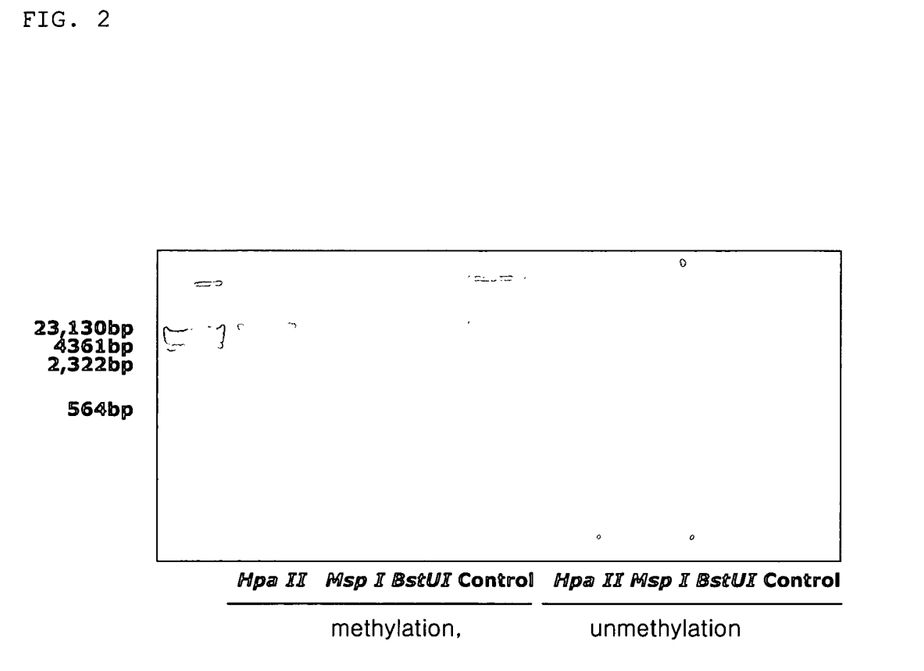
FIG. 2 is a picture showing that CG of *E. coli* chromosomal DNA is completely methylated. Restriction enzyme HpaII and BstUI digest unmethylated CG and MspI digests both methylated CG and unmethylated CG. In left panel, methylated DNA of the present invention is resistant to HpaII and BstUI thus is fully methylated.

The purified *E. coli* chromosomal DNA were treated with CpG methylase (M. Sss I; NEB M0226S) at the ratio of 1 unit/10 ug and performed the reaction at 37° C. for 12 hrs. At the reaction 160 uM of S-Adenosylmethionine as methyl donor was used. After methylation reaction, remaining salt and enzyme were removed by using DNA clean kit (CPG DPC60050) and micropure EZ (amicon 42529). The purified methylated DNA were treated with restriction enzyme Hpa II, Msp I or BstU I and confirmed whether the DNA are methylated or not through size change by restriction enzyme on agarose gel (see FIG. 2).

2-3: *E. coli* DNA Fragmentation

The purified *E. coli* chromosomal DNA having methylated CpG was dissolved in TE buffer solution to 0.5 mg/ml and sonicated in a glass beaker with ultrasonicator.

20 ml of the solution was fragmented at one time using 500 watt sonication VCX500 (Sonics Co.) as ultrasonicator and 630-0220 (tip diameter: ½" (13 mm)) as tip.

Figure 1:
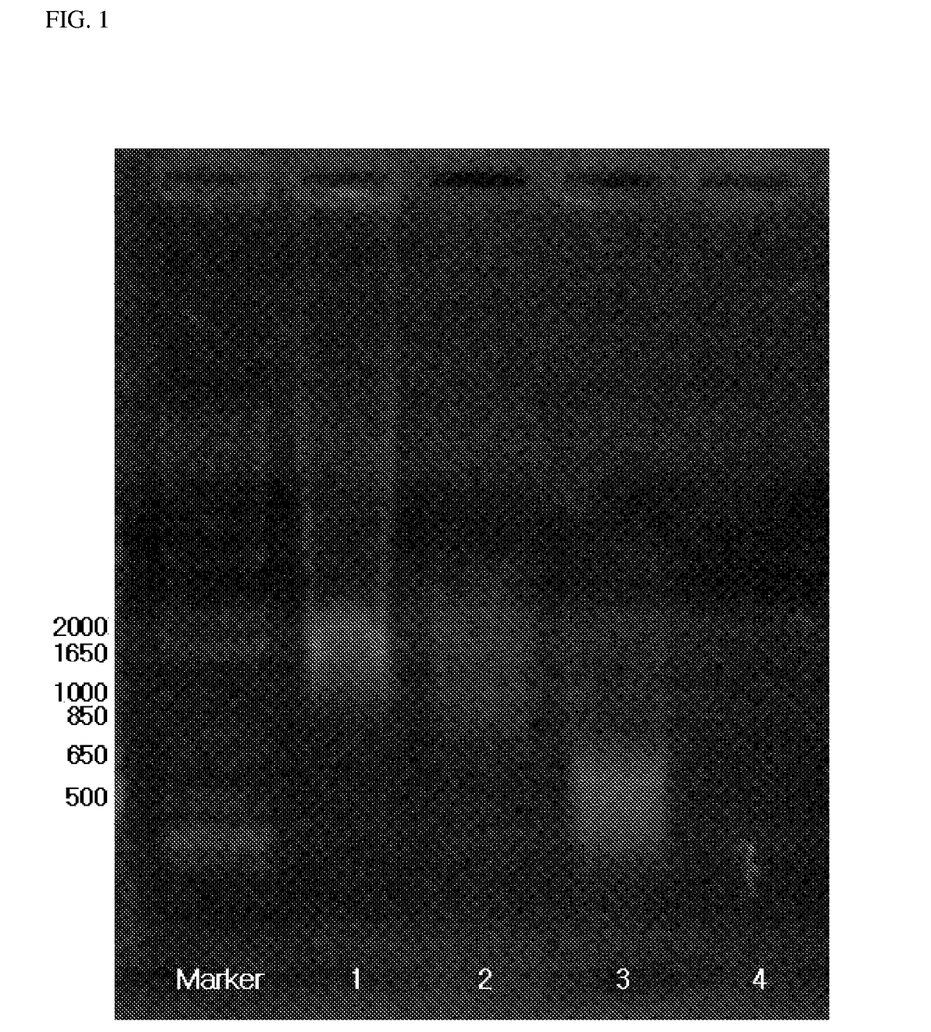
FIG. 1 is a picture illustrating *E. coli* chromosomal DNA divided into each fraction by using ultrasonicator to detect the size of *E. coli* DNA representing the optimal effect, wherein Lanes 1, 2, 3 and 4 represent intact (more than 10 kb), 2.0-0.5 kb, 0.5-0.1 kb and less than 0.1 kb of DNA, respectively.

Here, in order to identify the size of *E. coli* DNA representing the optimal effect, the whole *E. coli* chromosomal DNA was divided in 20,000 J according to time period using ultrasonicator and then separated by size (see FIG. 1). Methylated *E. coli* DNA was divided into the whole DNA (Intact, more than 10 kb), 2.0~0.5 kb, 0.5~0.1 kb and less than 0.1 kb according to its size before sonication.

Figure 3:
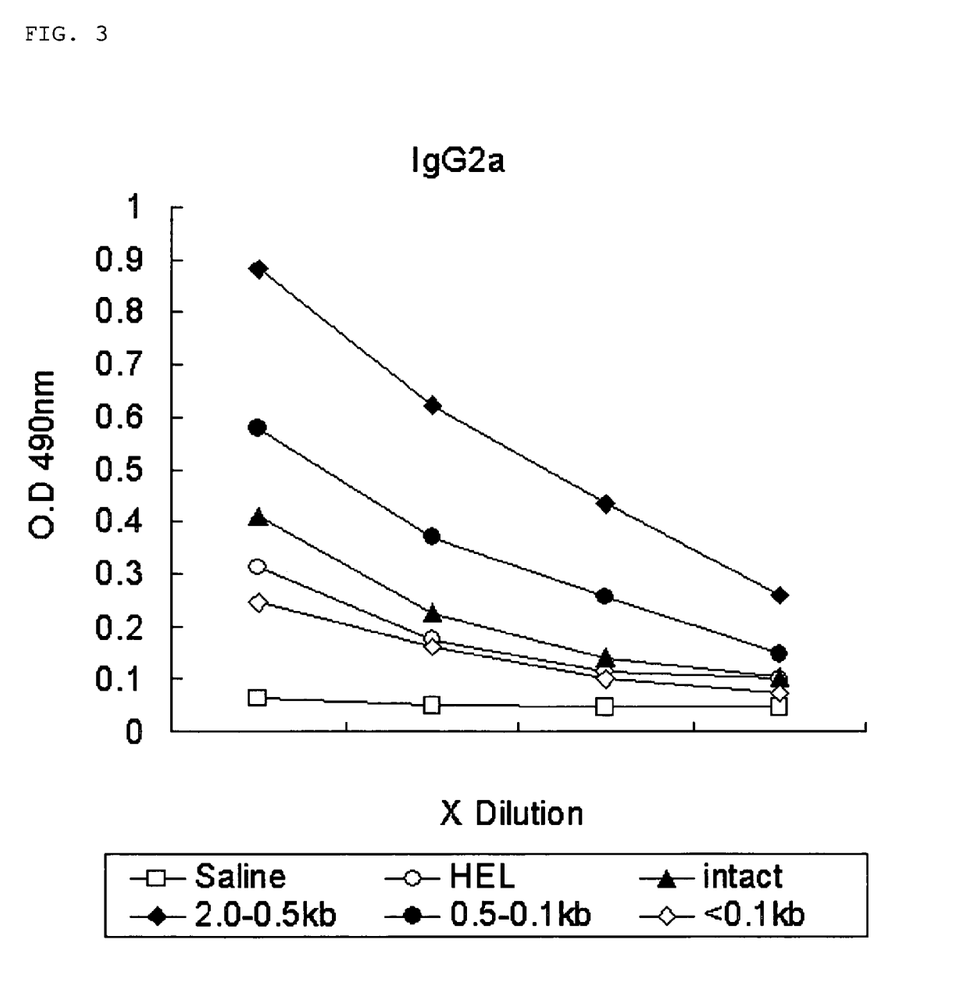
FIG. 3 is graphs illustrating the highest immune increasing effect in *E. coli* DNA (mCIA02) of about 2-0.5 kb.

In order to identify immune increase effects of *E. coli* DNA having methylated CpG separated according to size, the effect as immune adjuvant was measured in mouse (see FIG. 3). 50 ug of HEL (Sigma) as antigen and 50 ug of each *E. coli* DNA as adjuvant were injected (i.p) into ICR mouse (a 4-week old male, 20 g) twice at interval of a week. 7 days after final injection, the whole blood was collected and serum was separated. The antibody Ig G2a in serum was measured with HEL as antigen using ELISA method (see FIG. 3).

As analysis results, the size of 2.0–0.5 kb showed the highest antibody value. Thereafter, from repeated experiments, it was shown that about 1 kb represented the optimal effect.

The sonication condition for obtaining 1 kb E. coli DNA determined according to the above result is at 7 minutes in 20,000 J.

Example 3

Removal of Endotoxin from E. coli DNA and Measurement of DNA Purity

Removal of Endotoxin

After sonication, DNA was reacted with chloroform at 4° C. for 12 hours, and three volumes of ethanol was treated therein to obtain a precipitate.

The precipitate was treated with Triton X-114 (Sigma) to 0.5% of final concentration. The resulting precipitate was reacted at 4° C. for 4 hours, warmed at 37° C. for 5 minutes and then mixed with phenol/chloroform/isoamyl alcohol (25:24:1) at a ratio of 1:1 to obtain water layer.

The obtained E. coli DNA was precipitated with ethanol and dissolves in pyrogen free water.

Endotoxin removed DNA was analyzed with Limulus Amebocyte Lysate (LAL) kit (BioWhittaker QCL-1000) to detect the remaining endotoxin.

Table 1 shows the endotoxin value and yield of purified E. coli DNA (CIA02) after removal of endotoxin according to the above method.

TABLE 2

The endotoxin value and yield of purified E. coli DNA(CIA02)

| Sample Number | DNA Concentration | Amount of the whole DNA (/15 ml) | Pyrogen free DNA | Ratio | Endotoxin (per DNA 1 mg/ml) | Yield |
|---|---|---|---|---|---|---|
| 1 | 3 mg/ml | 45 mg | 16.2 mg | 1.77 | <1 ng | 36% |
| 2 | | | 20.25 mg | 1.66 | <1 ng | 45% |
| 3 | | | 18.9 mg | 1.71 | <1 ng | 42% |

The amount of remaining organic solvent was measured with GC/MSD (gas chromatography/mass selected detector), HP-5890A/HP-5870B. Ethanol, acetone, chloroform and penol were measured with SIM (Selected Ion Monitoring) having the column of 50 m.ultra-1 (see Table 2).

TABLE 3

Amount of remaining organic solvent

| Remaining organic solvent | Acetone | Ethanol | Phenol | Chloroform |
|---|---|---|---|---|
| ng/ul | — | 0.813 | — | — |

More than 99% degree of purity was identified by measuring protein contamination per E. coli DNA mg with Brad-Ford method.

Example 4

Purification of Lipopolysaccharide (CIA04) from Mutant E. coli

Purification of Lipopolysaccharide from Mutant E. coli
E. coli was prepared with the same method as above described DNA isolation method.

The prepared E. coli was mixed with 2 volumes of ethanol thereof, and centrifuged at 4,000 g to obtain a precipitate. 1.5 volumes of acetone of the precipitate was added, mixed and then centrifuged at 4,000 g.

The same amount of ethyl ether was added and mixed in the resulting precipitate, and then centrifuged at 4,000 g. The cell pellet obtained therefrom was covered with aluminum foil and punctured the foil and dried to measure cell mass. Thereafter, 7.5 ml of extraction mixture (90% penol:chloroform:petroleum ether=2:5:8) was added per 1 g of cellular dry weight.

The resulting solution was divided into glass centrifuge tube and centrifuged at 25° C., 3,000 rpm (1,200 g) for 20 minutes to obtain supernatant. The supernatant was left in hood for 12 hours. Then, the solution was divided into glass centrifuge tube and lipopolysaccharides dissolves in ethyl ether by centrifugation at 25° C., 3,000 rpm (1,200 g) for 20 minutes, and then transferred into eppendorf tube. The solution was dried in hood, and dried weight was measured with chemical balance. Then, ethanol was added therein and stored before use.

Figure 4:
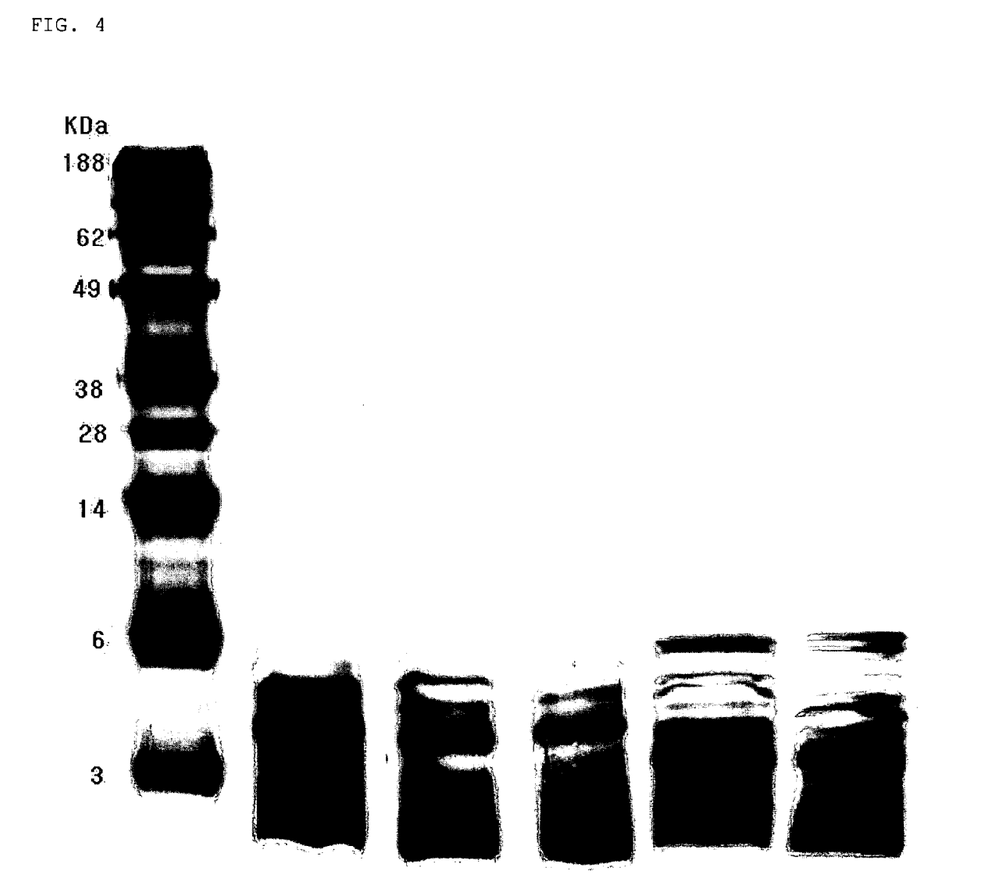
FIG. 4 is a picture illustrating lipopolysaccharide product isolated from *E. coli* outermembrane. The picture illustrates isolated lipopolysaccharide according to 5 times batch.

After ethanol was completely eliminated in purified E. coli lipopolysaccahride stored in ethanol, the amount of KDO (2-Keto-3-deoxyoctonate) in lipopolysacchardie was measured with lipopolysaccharide standard (Lsit Biological Lab.). After the concentration was measured from the standard, the lipopolysaccharides were analyzed with SDS-PAGE according to size and identified by silver staining (see FIG. 4). The lipopolysaccharide had molecular weight ranging from about 5,000 to 10,000, and its size was very small compared with general E. coli lipopolysaccharide.

Example 5

Removal of Toxicity in Purified Lipopolysaccharide from Mutant E. coli 5-1: Removal of Toxicity in Lipopolysaccharide by Lipid A Degradation Purified E. coli lipopolysaccharides diluted to 3 mg/ml of concentration and mixed with 0.2 N NaOH at a ratio of 1:1. The resulting solution was shaken every 10 minutes at 60° C. and deacylated for 140 minutes.

About 1/5 volumes of initial 0.2 N NaOH of 1N acetic acid was added in the resulting solution to titrate pH 7.0.

After pH titration, ethanol-precipitated non-toxic lipopolysaccharide was obtained.

After the concentration of non-toxic lipopolysaccharide was measured with KDO method, its size change was identified by SDS-PAGE and silver staining in comparison with lipopolysaccharide before treatment.

Figure 5:
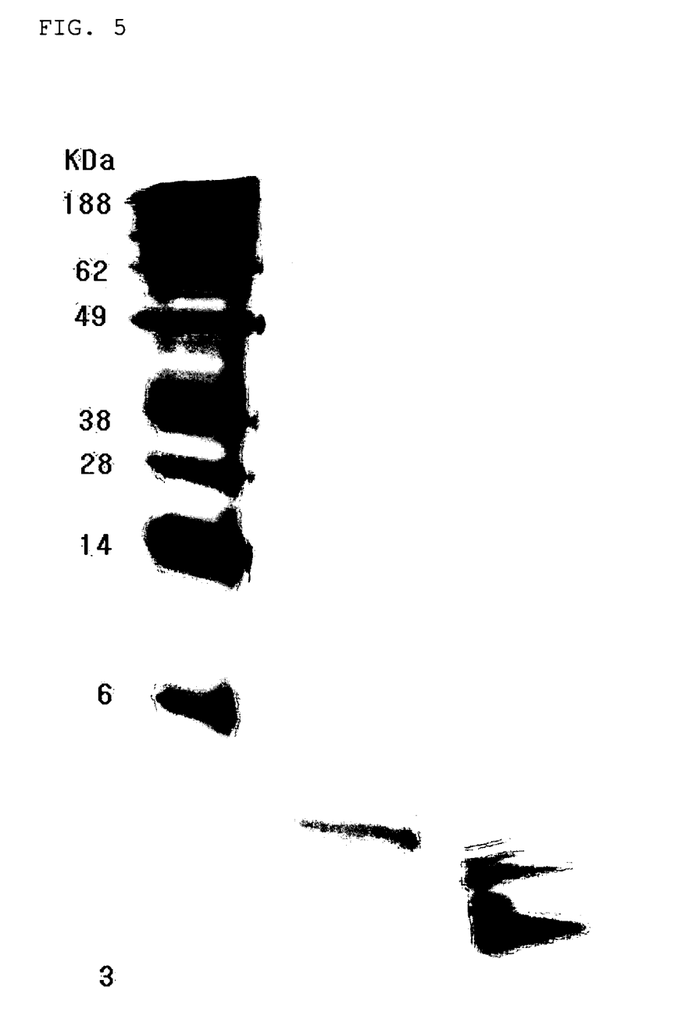
FIG. 5 is a picture illustrating that the size of isolated *E. coli* lipopolysaccharide treated with alkali is changed by degrading lipid A and lose toxicity by this treatment, wherein Lane 1 represents isolated lipopolysaccharide product CIA04 and Lane 2 alkali-treated non-toxic lipopolysaccharide CIA05.

As a result of staining, it was shown that lipid A of lipopolysaccharide was degraded by alkali treatment and the size of lipopolysaccharide became smaller (see FIG. 5).

5-2: Confirmation of Toxicity Removal of Non-Toxic Lipopolysaccharide

In order to test stability of non-toxic lipopolysaccharide, experiments on secretion, pyrogenicity and abnormal toxicity of inflammatory proteins were performed.

Experiment on Secretion of Inflammatory Protein

THP-1 (Acute monocytic leukemia) was treated with non-toxic lipopolysaccharide from high to low concentration to measure the amount of secreted TNF-α in comparison with the control group of purified lipopolysaccharide.

Figure 6:
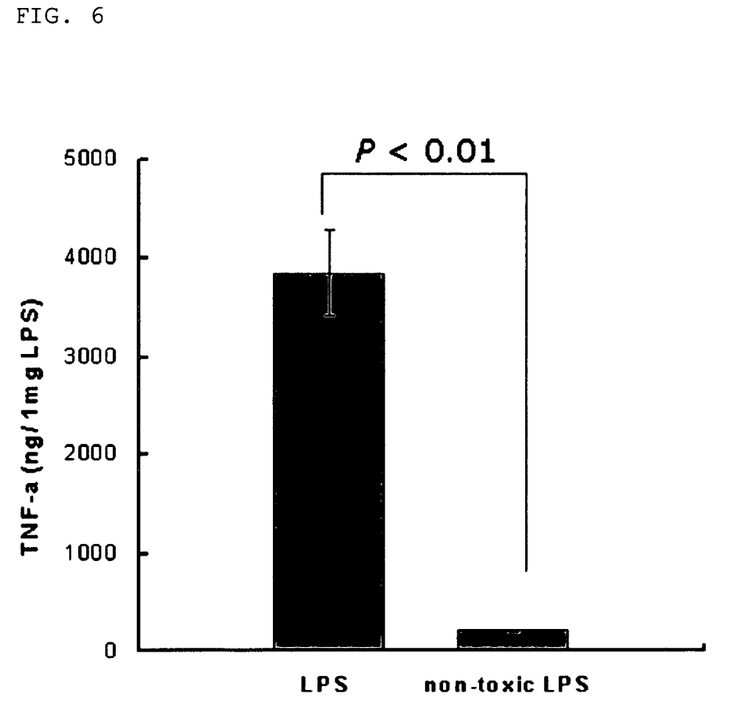
FIG. 6 is a graph illustrating the decrease of TNF-α secretion in THP-1 cell line treated with the non-toxic lipopolysaccharide (CIA05).

While 5 pg TNF-α was secreted in 1 ug of lipopolysaccharide in the control group, 0.1 pg TNF-α was secreted in 1 ug of non-toxic lipopolysaccharide. Here, it was shown that inflammatory reaction induced by toxicity decreased by 50 times. Additionally, it was shown that the amount of TNF-α secreted in *E. coli* DNA was below 100 fg. As a result, the non-toxic lipopolysaccharide was proved to be very safe material (see FIG. 6).

Experiment on General Safety Test maximum value of the difference in temperature was defined as pyrogen reaction of the experimental animals. Here, the samples of three animals were used.

Pyrogenic material experiment was negative when the total of three animals was below 1.3° C. while positive when over 2.5° C. These experiments were performed three times, and the negative reaction was suitable for these pyrogenic material experiments.

The results are shown in Table 4.

TABLE 4

| The No. of time | Number | Before injection (three times) | | | After injection (hrs) | | | | | | Increased body Temp. | Sum of increased body Temp. | Result | standard |
|---|---|---|---|---|---|---|---|---|---|---|---|---|---|---|
| | | 1 | 2 | 3 | 0.5 | 1 | 1.5 | 2 | 2.5 | 3 | | | | |
| 1 | 1 | 39.1 | 39.2 | 39.2 | 39.4 | 39.3 | 39.2 | 39.2 | 39.1 | 39.1 | 0.2 | 0.8 | pass | <1.3° C. |
|   | 2 | 39 | 39.1 | 39.3 | 39 | 39.2 | 39.5 | 39.2 | 39.1 | 39.3 | 0.4 | | | |
|   | 3 | 39.4 | 39.2 | 39.2 | 39.3 | 39.5 | 39.3 | 39.5 | 39.3 | 39.4 | 0.2 | | | |
| 2 | 1 | 39 | 39.3 | 39.1 | 39.4 | 39.2 | 39.3 | 39.1 | 39.2 | 39 | 0.4 | 1.7 | pass | <3.0° C. |
|   | 2 | 39.4 | 39.2 | 39.2 | 39.1 |  | 39.3 | 39.1 | 39.2 | 39.2 | 0.3 | | | |
|   | 3 | 39.3 | 39.3 | 39.2 | 39.4 | 39.4 | 39.4 | 39.4 | 39.3 |  | 0.2 | | | |
| 3 | 1 | 39.2 | 39.2 | 39.1 | 39.2 | 39.2 | 39 | 39.2 | 39.1 | 39.1 | 0.2 | 2.5 | pass | <5.0° C. |
|   | 2 | 39.1 | 39.5 | 39 | 39 | 39.1 | 39.2 | 39.1 | 39.3 | 39.2 | 0.4 | | | |
|   | 3 | 39.2 | 39.3 | 39.2 | 39.3 | 39.2 | 39.3 | 39.2 | 39.4 | 39.3 | 0.2 | | | |

The sample of high dose was injected in more than two kinds of rodents to observe abnormal weight change.

A. Experiment in Guinea Pig

About 350 g of a guinea pig showed no abnormality and gained weight gradually when observed for more than 5 days before use.

The 5 ml of sample was used per one guinea pig.

The sample was one time injected (i.p) into more than two guinea pigs, and they were observed for more than 5 days.

B. Experiment in Mouse

An about 5-week old mouse showed no abnormality and gained weight gradually when observed for more than 5 days before use.

The sample was one time injected (i.p) into more than two mice, and they were observed for more than 7 days.

The sample was proved suitable in this experiment when an animal showed no abnormality during the observation period.

Figure 7:
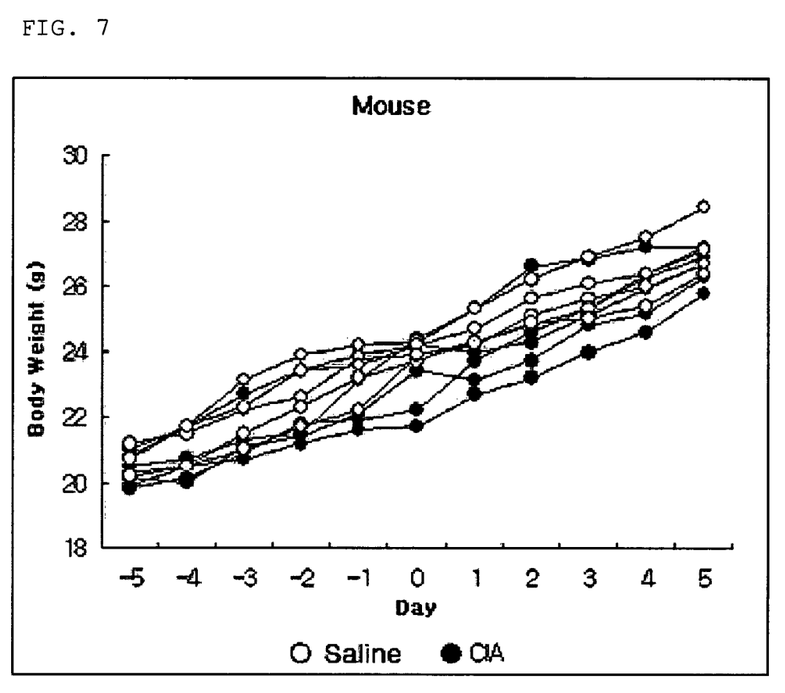
FIG. 7 is a graph illustrating results of general safety test on the non-toxic lipopolysaccharide (CIA05) in mouse.

As an experimental result, no abnormal weight change was observed after injection of the sample (see FIG. 7).

Pyrogenicity Experiment

After vaccine was injected into three rabbits, change in the rectal temperature was observed. The 0.2 ug/ml of sample per 1 kg of rabbit was injected in ear vein of rabbit. Then, the change in abnormal temperature was measured by inserting a thermometer into the rectum.

Here, the weight of rabbits was over 1.5 kg. The rabbits were reused more than 3 days after they had been used in experiments. The body temperature was measured with an apparatus measuring the temperature up to 0.1° C. An injector and its needle were heat-sterilized at 250° C. for over 30 minutes. Only water was fed from 16 hours before use to completion of the experiment. The animals were fixed not as tight as possible.

The body temperature was measured by inserting the thermometer into the rectum to a constant depth ranging from 60 to 90 mm for constant time. The temperature measured before injection was defined as a control temperature. The sample heated at 37° C. was injected into the ear vein within about 15 minutes after the control was measured. The body temperature was measured every 3 hours, at least 1 hour, after injection. Gap between the control temperature and sample temperature was defined as difference in temperature. The Example 6

Figure 8A:
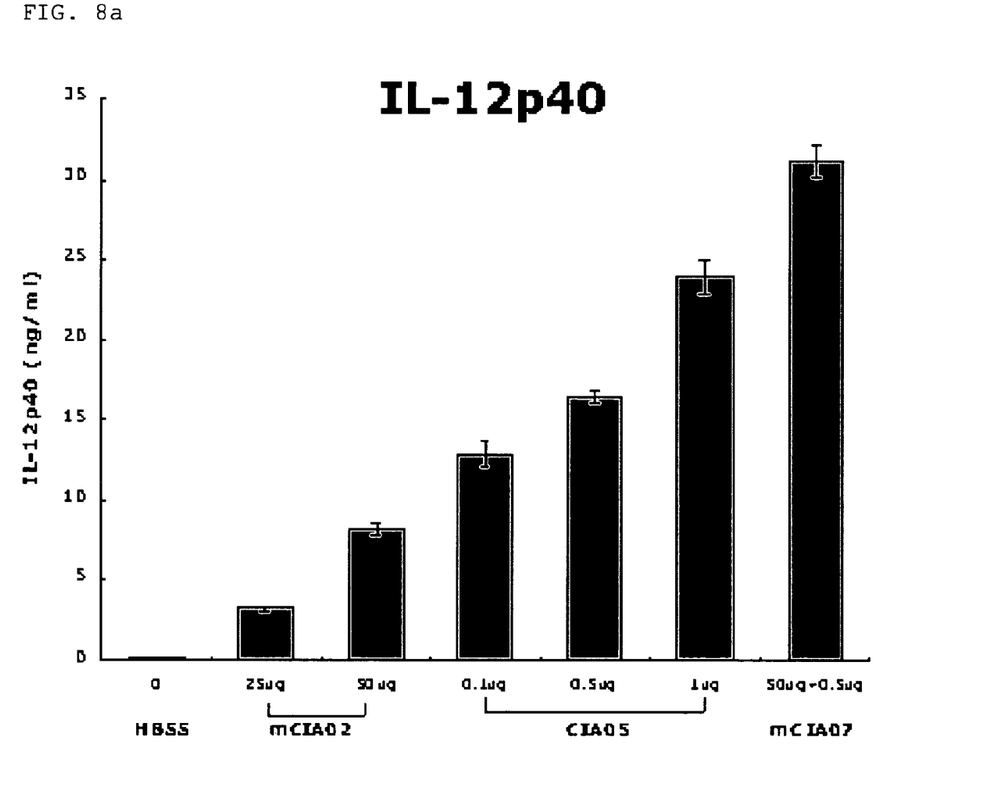
FIG. 8a to 8b are graphs illustrating the secretion amount of IL-12 p40 and TNF-alpha by methylated *E. coli* DNA (mCIA02), non-toxic lipopolysaccharide (CIA05) and mCIA07 (mCIA02+CIA05).
Figure 8B:
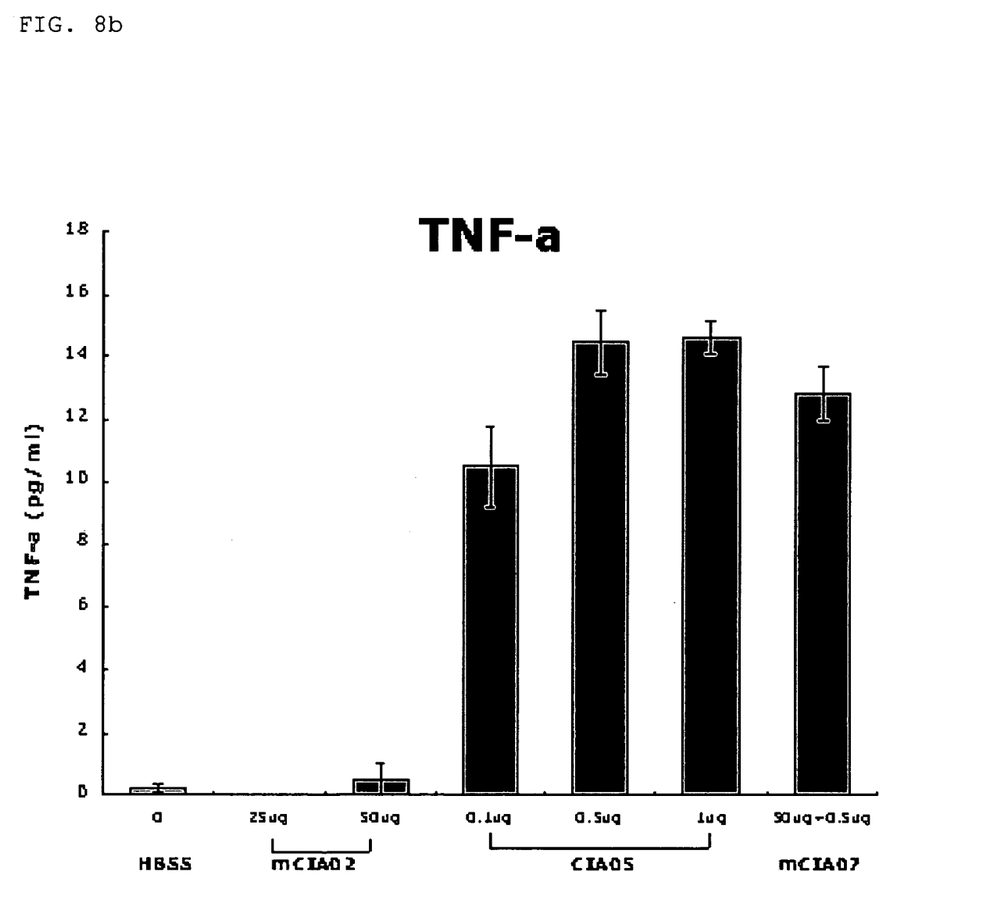

Mixing *E. coli* DNA Fragment Having Methylated CpG and Non-Toxic Lipopolysaccharide and Identification of Activity 6-1: Mixing *E. coli* DNA Having Methylated CpG (mCIA02) Fragment and Non-Toxic Lipopolysaccharide and Identification Activity with Whole Blood Analysis Venous blood from healthy male adult was sterilely obtained in vacuum tube having heparin as anticoagulant. The whole blood obtained therefrom was mixed with RPMI 1640 culture medium (2 mM L-glutamine, 1 mM Sodium pyruvate, gentamycin of 80 ug/ml) at a ratio of 1:1. 20 ul of mCIA07 50 ug of *E. coli* DNA having methylated CpG (mCIA02)+1 ug or 500 ng, 100 ng of CIA05) or 20 ul of HBSS were added in 1 ml of the whole blood mixed with culture medium and then incubated in 5% $CO_2$ culture medium at 37° C. for 24 hours. The secretion amount of TNF-alpha (R&D system, DY 210) and IL-12 p40 (R&D system, DY1240) was analyzed in supernatant liquid in the culture medium with ELISA kit. The results were shown in FIG. 8. The analysis results show that mCIA07 has the synergistic effect on immune response than separatively administrating mCIA02 or CIA05 (FIG. 8*a*) and mCIA07 has the lower toxicity than separatively administrating mCIA02 or CIA05 (FIG. 8*b*).

Figure 9:
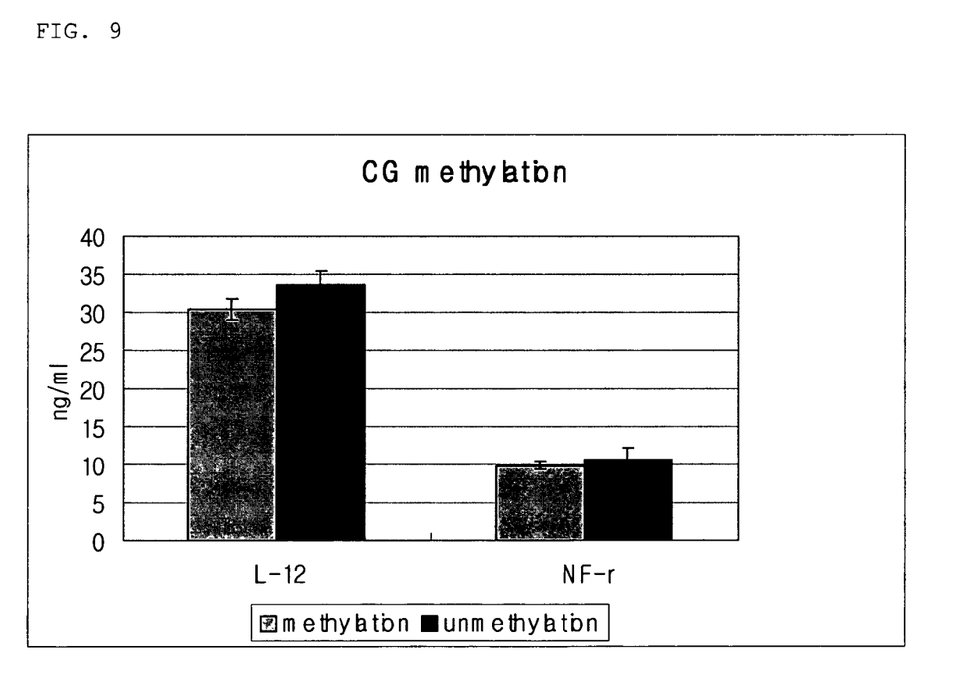
FIG. 9 is a graph showing immune response of mCIA07 and CIA07

6-2: Comparing Activity Between Methylated CG and Un Methylated CG of *E. coli* DNA 50 ug of 0.5-2.0 kb *E. coli* DNA having methylated CpG obtained from example: 2-2 (methylation process) or 50 ug of 0.5-2.0 kb of unmethylated CG of *E. coli* DNA were mixed with 1 ug of CIA05 to prepare mCIA07 and CIA07 respectively. According to method described in example: 6-1 resulting mCIA07 or CIA07 were carried out whole blood analysis. The amount of IL12 and IFN-gamma were almost same irrespective of methylated DNA or unmethylated DNA (see FIG. 9).

Example 7

Measurement of Anti-Cancer Treatment Effect Using Cell Lysis Activity of Composition of the Present Invention Cancer cell killing activity by the present composition was measured using $_{51}$Cr-release.

Antigen only or with mixture of *E. coli* DNA fragment+ nontoxic LPS was injected under the skin of the bottom of the foot of a 5~8 week old male C3H/HeN mouse.

RPMI-1640 (10 mM HEPES, 100 units/ml penicillin, 100 μg/ml streptomycin, 300 μg/ml glutamine; Gibco Laboratories, Grand Island, N.Y.) was used for the basal culture medium for culturing cell lines. Inactivated 10% fetal bovine serum (Gibco Laboratories, Grand Island, N.Y.) heated at 56° C. for 30 minutes was added in the basal culture medium. In order to measure activity of LAK cells and cancer cell mediated killing activity, Sarcoma 180 and mouse bladder cancer cell line (MBT-2) were used for target cells.

In order to prepare reaction cell lines, a rat of the experimental group were killed using cervical dislocation. Its spleen was sterilely isolated and minced on stainless steel wire netting using scissors. The fragments were ground and filtered using a glass stick with adding phosphate buffered saline. Then, tissue debris was removed passing through wire netting. After single cell suspension was identified under microscope, cells were washed using the basal culture medium one time. The cells were suspended in 0.84% ammonium chloride solution at 37° C. for 5 minutes to dissolve erythrocyte. The cells were further washed using the basal culture medium two times and suspended in complete culture medium. The cell suspension was divided into culture flasks and cultured in $CO_2$ constant temperature and humidity chamber at 37° C. for 1 hour. Cells that were not attached to the flasks were obtained therefrom, and survival cell number was measured using trypan blue dye exclusion method. Then, $5\times10^6$ cells were obtained using the complete culture medium and survival cell number thereof was measured using trypan blue dye exclusion method. Then, $5\times10^6$ cell/ml of cell suspension were made using the complete culture medium.

Target cell line was cultured and the number of cells was counted. $10^6$ cells were obtained and the cells were centrifuged at 300 g, 3 minutes. The supernatant liquid except 0.2~0.3 ml was removed using Pasteur pipette without damaging precipitated cells. 100 Ci $Na_{2\ 51}CrO_4$ (1 ml Ci/ml, NEZ 030S, NEN, USA) was added and labeled in shaking thermostat at 37° C. for 1 hour. The cells were washed using the basal culture and survival cell number thereof was measured using trypan blue dye exclusion method. The labeled target cells were re-suspended in the complete culture medium to $5\times10^4$ cell/ml.

The labeled target cells were divided by 0.1 ml to put $5\times10^3$ cells per a well on 96 well fine plate having a round bottom. 0.1 ml of reactions cell was added at a ratio of reaction cell:target cell=100:1. The cells were cultured in 5% $CO_2$ constant temperature and humidity chamber at 37° C. for 4 hours. After more than 3 wells per an experiment were made and the culture for 4 hours was finished, the cells were centrifuged at 500 g for 15 minutes. Radioactivity was measured in the 0.1 ml of supernatant liquid from each well using gamma counter (Packard, USA). Here, in order to induce the maximum emission, 0.1 ml of 5% triton X-100 (Sigma, USA) was added in the control well group. In order to measure natural emission, the labeled cells were cultured in the complete culture medium having the same dose. The cell toxicity was calculated according to the following formula:

Cytotoxicity(%)=(ER−SR/MR−SR)×100

ER: average count (cpm) of experiment group

SR: average count (cpm) target cell cultured in culture medium

MR: average count (cpm) of target cell treated with 5% Triton X-100.

The experimental results were shown in Table 5. LAK cells showed cell lysis increase by 8 times in comparison with non-immune cells, and by 1.5 times in comparison with BCG injection group. MBT-2 cell line showed cell lysis increase by 5 times in comparison with non-immune cells. These results represent possibility of the composition for anti-cancer treatments instead of BCG resulting in various side effects.

TABLE 5

| | Injection days | | | |
|---|---|---|---|---|
| | 0 | 3 | 7 | 15 |
| Sarcoma 180 | | | | |
| Control group | 100 | 100 | 100 | 100 |
| BCG | 92 ± 4 | 110 ± 2 | 632 ± 13 | 189 ± 4 |
| Composition of the present invention | 94 ± 7 | 154 ± 3 | 802 ± 10 | 109 ± 7 |
| MBT-2 | | | | |
| Control group | 100 | 100 | 100 | 100 |
| BCG | 103 ± 3 | 96 ± 7 | 402 ± 11 | 98 ± 3 |
| Composition of the present invention | 97 ± 4 | 121 ± 9 | 513 ± 13 | 109 ± 6 |

INDUSTRIAL APPLICABILITY

The anti-cancer treatment mCIA07 of mixing two *E. coli* derived materials mCIA02 and CIA05 according to the present invention has higher safety than the conventional treatment and minimizes production cost due to simplicity of production process. Also, mCIA07 induces more effective and specific immunization due to mixing the two materials. Additionally, the present invention is cheaper than CpG due to physical process of DNA and more effective than BCG.

Accordingly, the *E. coli* derived anti-cancer treatment mCIA07 according to the present invention is more significant in industrial application for anti-cancer treatment and immune adjuvant.

What is claimed is:

1. An immune stimulating composition comprising:
   a) bacterial DNA fragments; and
   b) non-toxic bacterial lipopolysaccharides, wherein CpG sequences of bacterial DNA fragments are methylated, wherein the bacterial DNA fragments have size ranging from 0.5 kb to 2.0 kb and exclude unmethylated CpG, and wherein the non-toxic bacterial lipopolysaccharides are *Escherichia coli* lipopolysaccharides or mycobacteria lipopolysaccharides, have size ranging from 3,000 to 10,000 daltons, and have a degraded lipid A;
   wherein the degraded lipid A is produced from non-degraded lipid A by treatment with an alkaline; and wherein the non-toxic bacterial lipopolysaccharides produce an inflammatory reaction that is at least 50 fold less than an inflammatory reaction produced by control lipopolysaccharides.

2. The composition according to claim 1, wherein the weight ratio of a) and b) ranges from 500:1 to 1:500.

3. The composition according to claim 1, wherein the a) and the b) are mixed by shaking.

4. The composition according to claim 1, wherein the composition can be used as immune adjuvant.

5. The composition according to claim 1, wherein the bacterial DNA fragments are is *Escherichia coli* DNA fragments or mycobacteria DNA fragments.

6. The composition according to claim 5, wherein the bacteria is *Escherichia coli*.

7. The composition according to claim 6, wherein the *Escherichia coli* is *E. coli* EG0021 having deposit accession number KCCM-10374.

8. An immune stimulating composition comprising:
a) bacterial DNA fragments; and
b) non-toxic bacterial lipopolysaccharides, wherein the bacterial DNA fragments have size ranging from 0.5 kb to 2.0 kb and exclude unmethylated CpG, and wherein the bacterial lipopolysaccharides are *Escherichia coli* lipopolysaccharides or mycobacteria lipopolysaccharides, have size ranging from 3,000 to 10,000 daltons, and have a degraded lipid A;
wherein the degraded lipid A is produced from non-degraded lipid A by treatment with an alkaline; and
wherein the bacterial lipopolysaccharides are obtained from attenuated bacteria.

9. An immune stimulating composition comprising:
a) *Escherichia coli* DNA fragments; and
b) non-toxic *Escherichia coli* lipopolysaccharides, wherein the *Escherichia coli* DNA fragments have size ranging from 0.5 kb to 2.0 kb and exclude unmethylated CpG; wherein the non-toxic *Escherichia coli* lipopolysaccharides have size ranging from 3,000 to 10,000 daltons, and have a degraded lipid A; and wherein the composition induces immune activation T helper 1 type;
wherein the degraded lipid A is produced from non-degraded lipid A by treatment with an alkaline and
wherein the non-toxic *Escherichia coli* lipopolysaccharides produce an inflammatory reaction that is at least 50 fold less than an inflammatory reaction produced by control lipopolysaccharides.

10. An immune stimulating composition comprising:
a) *Escherichia coli* DNA fragments; and
b) non-toxic *Escherichia coli* lipopolysaccharides, wherein the *Escherichia coli* DNA fragments have size ranging from 0.5 kb to 2.0 kb and exclude unmethylated CpG; wherein the *Escherichia coli* lipopolysaccharides have size ranging from 3,000 to 10,000 daltons and have a degraded lipid A; and wherein the composition induces immune activation T helper 1 type;
wherein the degraded lipid A is produced from non-degraded lipid A by treatment with an alkaline; and
wherein the non-toxic *Escherichia coli* lipopolysaccharides produce an inflammatory reaction that is at least 50 fold less than an inflammatory reaction produced by control lipopolysaccharides.

* * * * *